United States Patent [19]

Calvo

[11] Patent Number: 5,618,288
[45] Date of Patent: Apr. 8, 1997

[54] STEREOTACTIC SYSTEM FOR SURGICAL PROCEDURES

[76] Inventor: Antonio M. Calvo, Rua Orense, 396, Diadema, Sao Paulo, SP, Brazil

[21] Appl. No.: 589,284

[22] Filed: Jan. 22, 1996

[51] Int. Cl.$^6$ ............................................. A61B 19/00
[52] U.S. Cl. ................................................. 606/130
[58] Field of Search ................................ 606/130, 129, 606/131

[56] References Cited

U.S. PATENT DOCUMENTS

| | | | |
|---|---|---|---|
| 3,061,936 | 11/1962 | Dobbeleer | 606/130 |
| 4,228,799 | 10/1980 | Anichkov et al. | 606/130 |
| 4,350,159 | 9/1982 | Gouda | 606/130 |
| 4,618,978 | 10/1986 | Cosman | 606/130 |
| 4,638,798 | 1/1987 | Shelden et al. | 606/130 |
| 4,722,336 | 2/1988 | Kim et al. | 606/130 |
| 5,163,430 | 11/1992 | Carol | 606/130 |
| 5,176,689 | 1/1993 | Hardy et al. | 606/130 |

FOREIGN PATENT DOCUMENTS 195595  5/1967  U.S.S.R. ............................. 606/130

*Primary Examiner*—Robert A. Hafer
*Assistant Examiner*—Justine Yu
*Attorney, Agent, or Firm*—Michael J. Striker

[57] ABSTRACT

The stereotactic system for surgical procedures includes a frame (3a) or ring (3b) securable to a head of a patient with a plurality of fixing screws (3s); a vertical bar bracket (3c) releasably attachable to the frame (3a) or ring (3b) to set a predetermined X or Y position; a vertical graduated bar (3d) movably engaged with, but securable to, the vertical bar bracket (3c), to set a predetermined Z position; a graduated tube (3e) fixed to and extending perpendicularly from the graduate bar (3d); a circular arc-shaped member (3f) provided with an angular positioning scale (AS) graduated in degrees, releasably securable to and pivotally mounted on the graduated tube (3e) and a surgical holding and guiding device securable at a predetermined angular position on the circular arc-shaped member (3f).

5 Claims, 6 Drawing Sheets

STEREOTACTIC SYSTEM FOR SURGICAL PROCEDURES

BACKGROUND OF THE INVENTION

The present invention relates to a stereotactic system for surgical procedures, particularly in the cephalic and cervical regions.

A stereotactic system for surgical procedures requiring penetration of the skull is known and consists of an advanced mechanical system made with materials which allow its sterilization at high temperatures. It is used to provide surgical access to brain tumors, for biopsies, for draining hematoma, for aspiration of encephalitic cysts, for implantation of stimulant electrodes, for endoscopy, for radiosurgery and other surgical interventions in the cephalic region in which exact localization and access are indispensable.

These surgical procedures using the stereotactic system are generally guided by magnetic resonance imaging (MRI), by computerized tomography(CT), by angiography or X-ray techniques with the help of a position determining or referential device based on a cartesian coordinate system.

Because of the growth in the stereotactic surgery field and the necessity of using the stereotactic system with great precision, a more versatile and accurate stereotactic system is necessary.

The improved stereotactic system however must be easy to use so that the possibility of doctor error is reduced and fast accurate positioning is possible. Furthermore the improved stereotactic system must be compatible with all modern imaging systems.

SUMMARY OF THE INVENTION

It is an object of the present invention to provide an improved stereotactic system which is more versatile and accurate than stereotactic systems of the prior art.

It is another object of the present invention to provide a more versatile and accurate stereotactic system which is easier to use, which minimizes doctor error, which provides a fast mounting and which is compatible with all modern imaging systems.

According to the present invention, the stereotactic system for surgical procedures includes a circular arc-shaped member provided with an angular positioning scale graduated in degrees, preferably to 0.1 mm precision; means for releasably securing the circular arc-shaped member to a head of a patient at a plurality of positions in relation to the head and means for releasably holding a surgical tool at a position along the circular arc-shaped member determined by the positioning scale.

The stereotactic system according to the invention has the advantage of being isocentric, thus eliminating complex computations to determine the location within the skull which must be reached in the surgical procedure, simplifying its use and reducing training time for professional medical personnel who must use the stereotactic system.

In a preferred embodiment of the stereotactic system of the invention the means for releasably securing the circular arc-shaped member to the head includes a substantially square frame having dimensions and provided with fixing screws so that the frame is releasably securable to the head, the frame having a scale graduated in millimeters along one side thereof. This embodiment of the system also includes a vertical bar bracket releasably secured to the side of the frame having the scale graduated in millimeters to set a X or Y coordinate position for the surgical procedure; and a vertical graduated bar attached releasably to the vertical bar bracket, having a positioning scale graduated in millimeters; a graduated tube attached to the vertical graduated bar and protruding perpendicularly from the vertical graduated bar and means for pivotally mounting the circular arc-shaped member to the graduated tube and for releasably positioning the circular arc-shaped member along the graduated tube to set a Z coordinate position for the surgical procedure.

In another preferred embodiment of the stereotactic system of the invention the means for releasably securing the circular arc-shaped member to the head includes a substantially circular ring having dimensions and provided with screws so that the ring is releasably securable to the head, and a graduated ruler connected to one side of the ring and having a scale graduated in millimeters for positioning to set a X or Y coordinate position. The system in this embodiment also includes a vertical bar bracket releasably secured to the graduated ruler to set X or Y coordinate positions for the surgical procedure; a vertical graduated bar attached releasably to the vertical bar bracket, the vertical bar bracket having a positioning scale graduated in millimeters; a graduated tube attached to the vertical graduated bar and protruding perpendicularly from the vertical graduated bar and means for pivotally mounting the circular arc-shaped member to the graduated tube and for releasably positioning the arc-shaped member along the graduated tube to set a Z coordinate position for the surgical procedure.

The stereotatic system also includes a reference device including a plurality of radiopaque plates provided with diagonal lines and means for holding these plates around the head of the patient during an MRI or CT procedure to determine the location of a feature in the head so as to eliminate complex mathematical calculations of the location of the feature. Advantageously the plates are approximately square and each plate has a scored diagonal depression or groove line extending at a 45° angle to one of its sides.

The means for releasably securing a surgical tool to a position along the semi-arch advantageously can be a slider for holding a cannula, a retractor spatula, an arch for guided surgery or a laser tool. The slider can also hold a skull drill and can have means for guiding the skull drill. The system can also advantageously be provided with means for holding at least one instrument for installing radioactive isotopes, means for holding at least one tube for guided surgery and means for holding at least one spatula for guided surgery.

In another embodiment the means for releasably securing the semi-arch to the head of the patient includes extension bars for increasing free space in the vicinity of the head.

BRIEF DESCRIPTION OF THE DRAWING

The objects, features and advantages of the present invention will now be illustrated in more detail by the following detailed description, reference being made to the accompanying drawing in which.

DESCRIPTION OF THE PREFERRED EMBODIMENT

Figure 4:
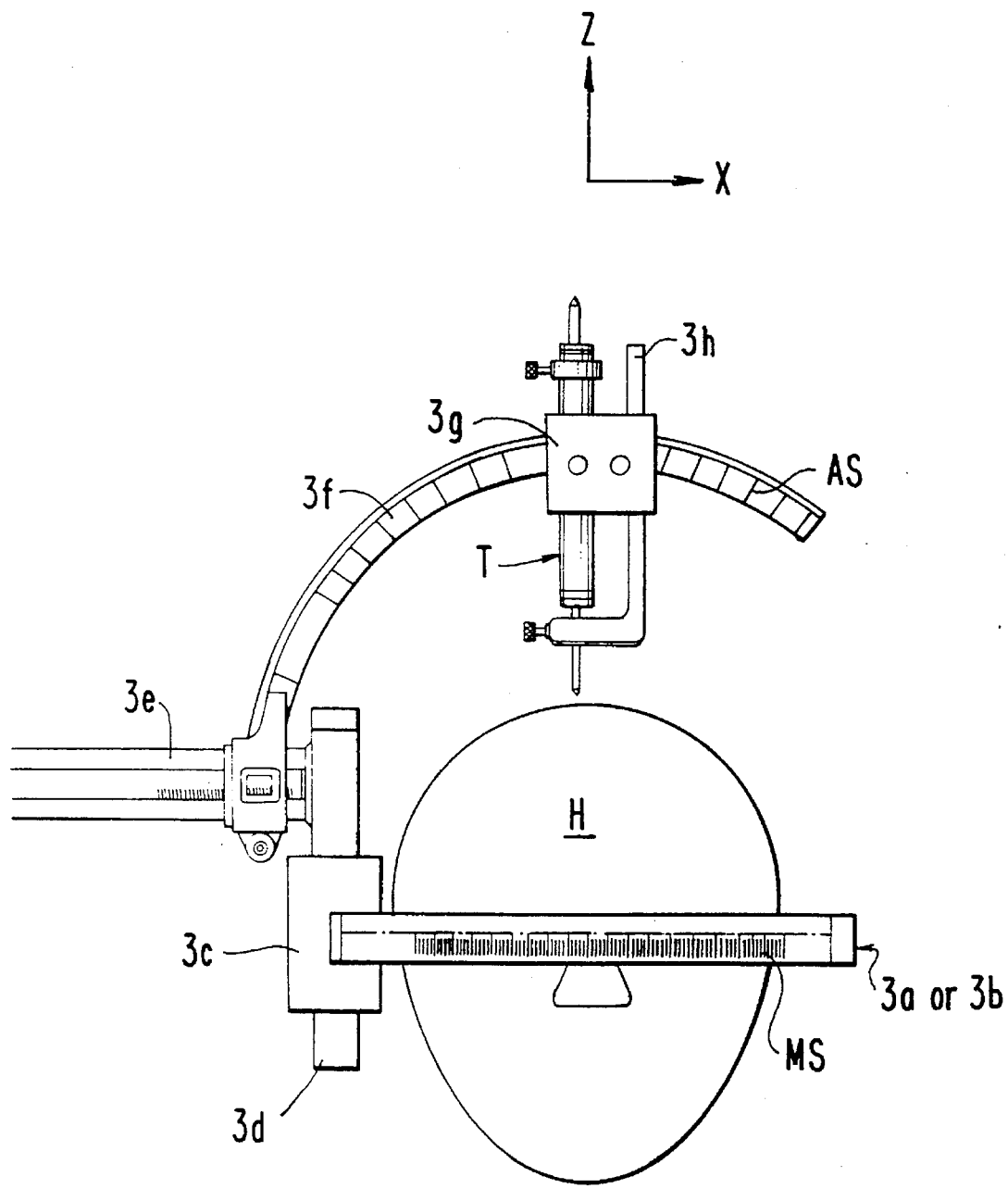
FIG. 4 is a diagrammatic side view of two embodiments of a stereotactic system according to the invention.

A stereotactic system according to the invention is shown in the drawing. This system comprises a frame 3a or a ring 3b which fixes the stereotactic system on the patient's head H by means of fixing screws 3s and a vertical bar bracket 3c which is releasably attached to the frame 3a or the ring 3b (see FIGS. 4 and 7). When the vertical bar bracket 3c is released it can be moved along a graduated scale MS, which is provided with millimeter divisions to permit its accurate positioning on the device for releasable attachment to the patient's head, i.e. either the frame 3a or the ring 3b, at the correct X or Y coordinate position required for the surgery.

Figure 5:
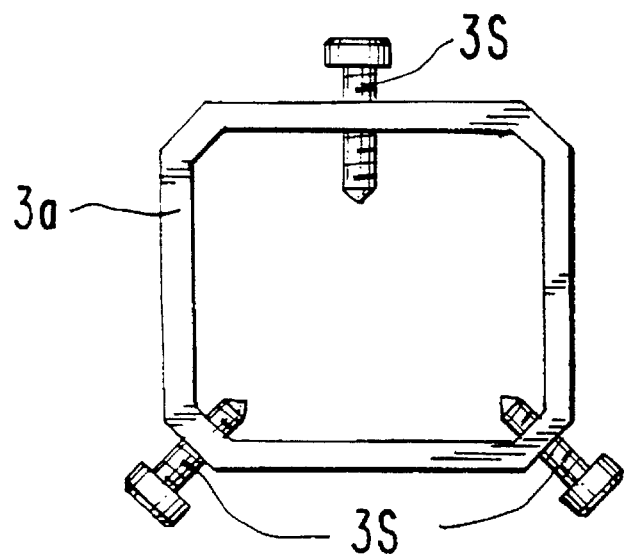
FIG. 5 is a top plan view of a square frame device for securing the stereotactic system according to FIG. 4 to the head.
Figure 6:
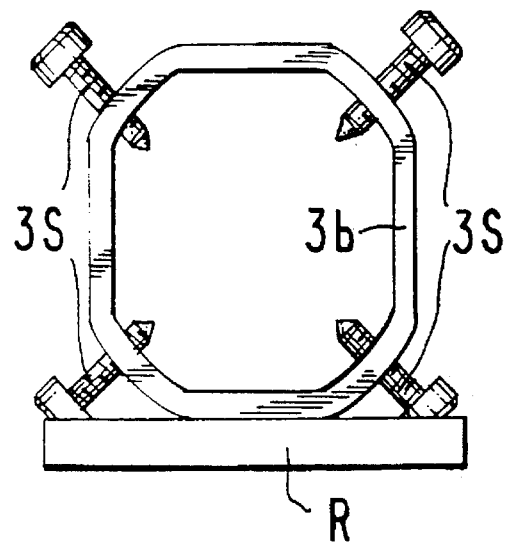
FIG. 6 is a top plan view of a ring device for securing the stereotactic system according to FIG. 4 to the head.

In one embodiment (see FIG. 5) the frame 3a is an approximately square single piece part provided with the graduated scale MS on one of its sides. This embodiment is comparatively costly to manufacture because of its complexity. In another embodiment (see FIG. 6) the device for releasable attachment of the stereotactic system is a ring 3b and a separately attachable ruler R provided with a graduated scale with millimeter divisions. This embodiment has a lower production cost and provides the same precision as the frame 3a. The ring 3b was a later improvement of the frame 3a and at any one time the stereotactic system is used with one or the other.

The system in both embodiments (FIGS. 4, 5 and 6) includes a vertical graduated bar 3d engaged in the vertical bar bracket 3c, whose function is to fix the Z coordinate position to a predetermined value and to support a graduated tube 3e having a scale with millimeter divisions. The graduated tube 3e is used as a pivot mount for a circular arc-shaped member 3f.

The circular arc-shaped member 3f is provided with an angular positioning scale AS having decimillimeter (0.1 mm) divisions. The circular arc-shaped member 3f is pivotally mounted and releasably securable on the graduated tube 3e and measures or sets the X/Z or Y/Z angle value (depending on where the vertical bar bracket is positioned).

Figure 8:
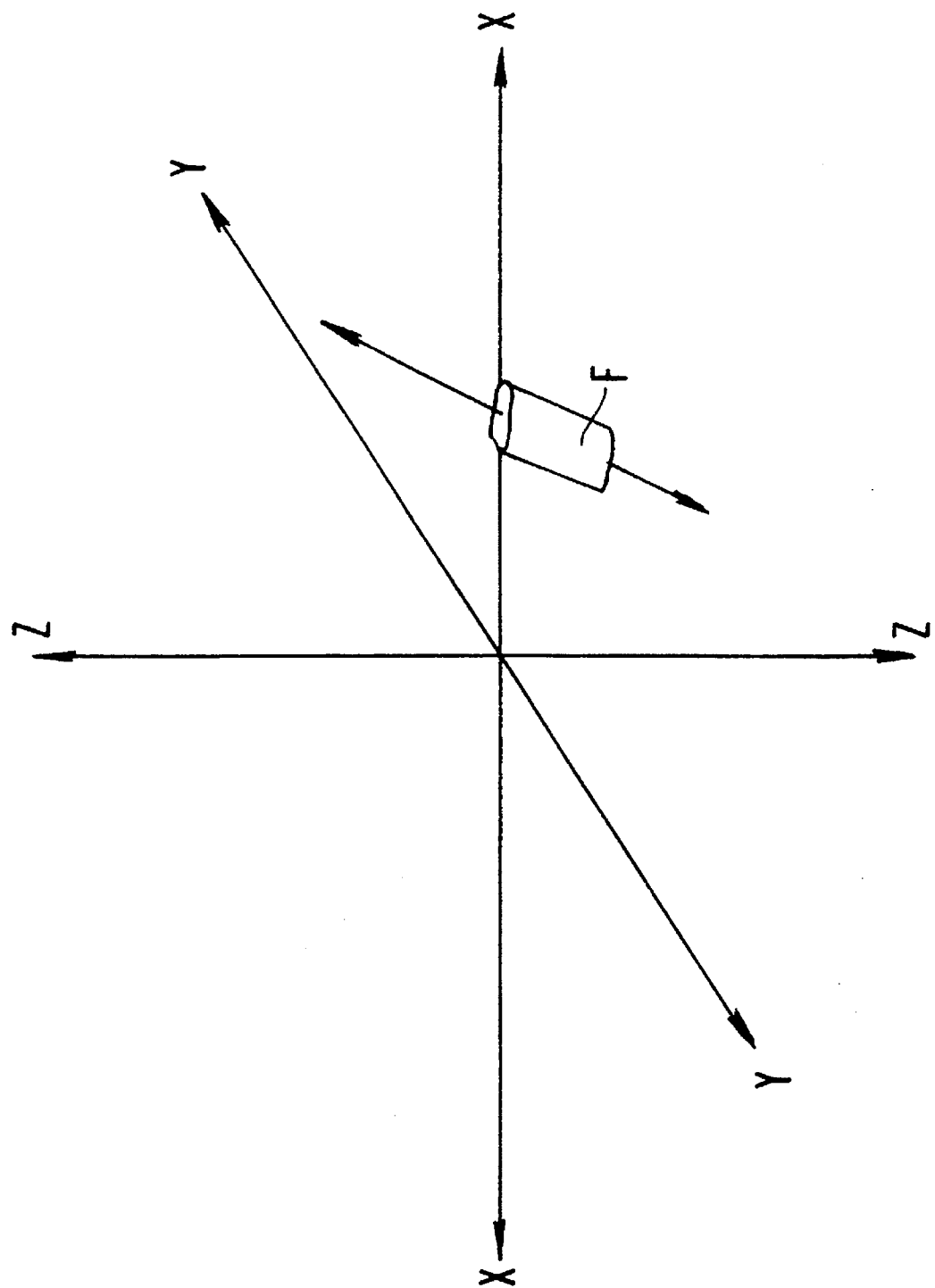
FIG. 8 is a diagrammatic perspective view showing a three dimensional feature, in this case a cylindrical shaped tumor, located on the cartesian axes of the stereotactic system.

The circular arc-shaped member 3f has slider 3g which is releasably attached to it. The slider 3g is provided with means for holding a surgical tool T and means for guiding it in operation 3h. The slider 3g has means for releasably securing it to an angular position measured by the angular positioning scale AS at a Y/Z or X/Z angle value (depending on where the vertical bar bracket is positioned). These angular degrees of freedom permit the tool to reach positions in spatial regions in the head which are not spherical, such as a cylindrical shaped tumor oriented in an oblique position relative to the three (X, Y, Z) axes (see FIG. 8), particularly they allow a tool motion across it from top to bottom.

The slider 3g can hold a variety of surgical tools T including a cannula, an endoscope, a laser ray tool and it is movable to different positions along the circular arc-shaped member 3f when released. The slider 3g supports the cannula, an endoscope, a laser ray tool and the like and allows it to be precisely positioned as determined by graduated scales with the millimeter divisions and with an additional vernier scale on its own body to a precision of 0.1 mm.

Figure 7:
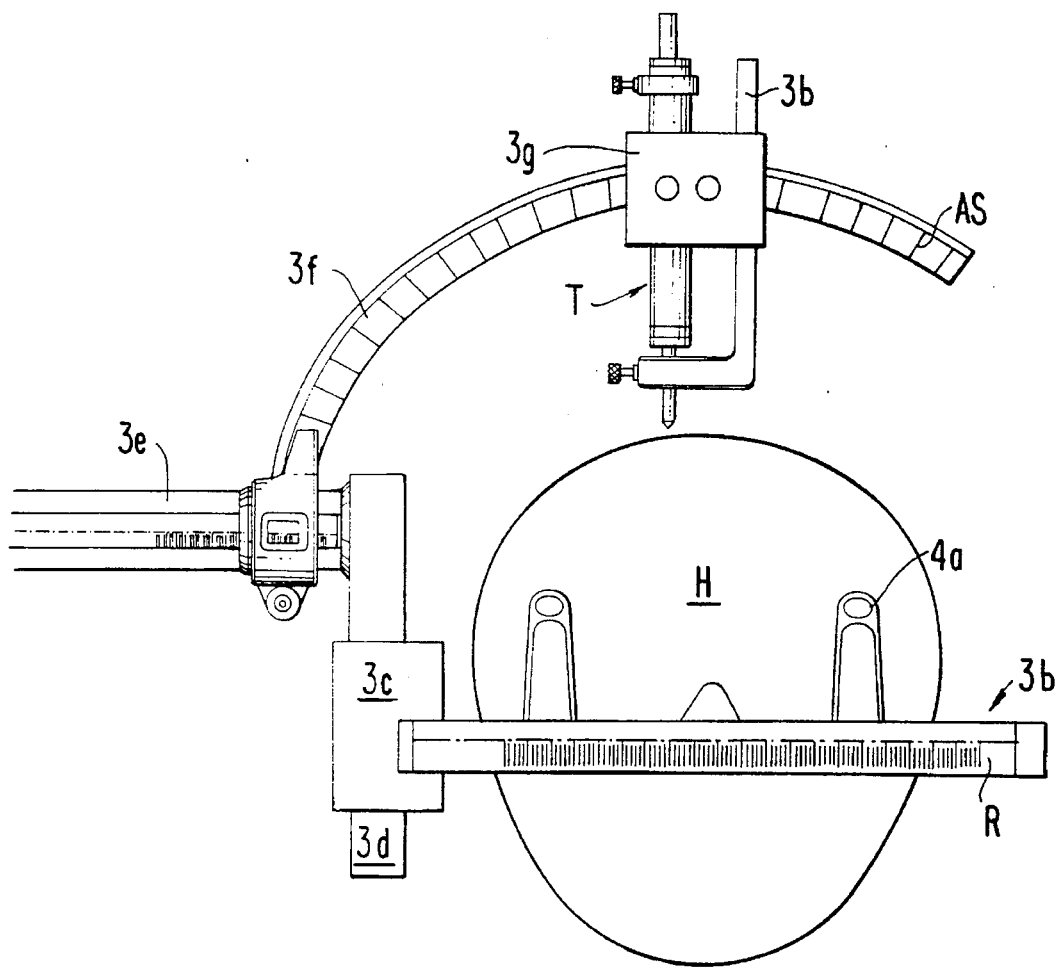
FIG. 7 is a diagrammatic side view of another embodiment of a stereotactic system according to the invention with extension bars to provide additional space in the vicinity of the head.

Another embodiment of the stereotactic system is shown in FIG. 7. In this embodiment the device for fixing the system to the head H has extension bars 4a which allow the positioning of the entire system at a lower position relative to the head to provide more free space or working area.

Figure 1:
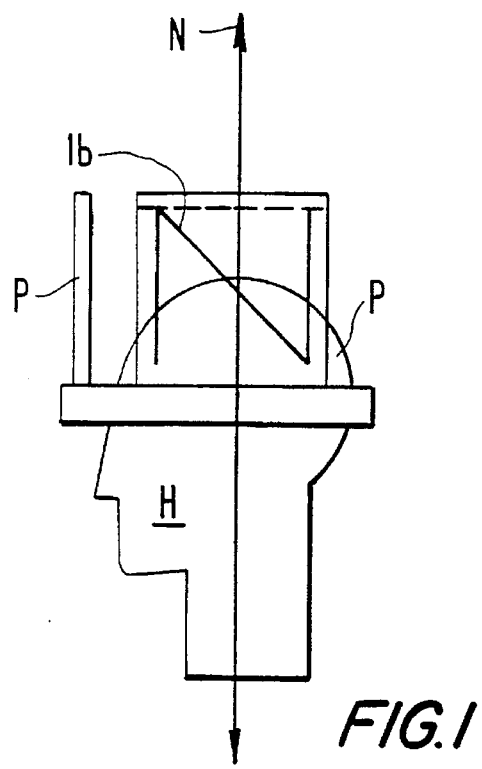
FIG. 1 is a diagrammatic side view showing radiopaque plates of a referential device for determining a position of a point or feature within the head or skull based on a cartesian coordinate system.
Figure 2:
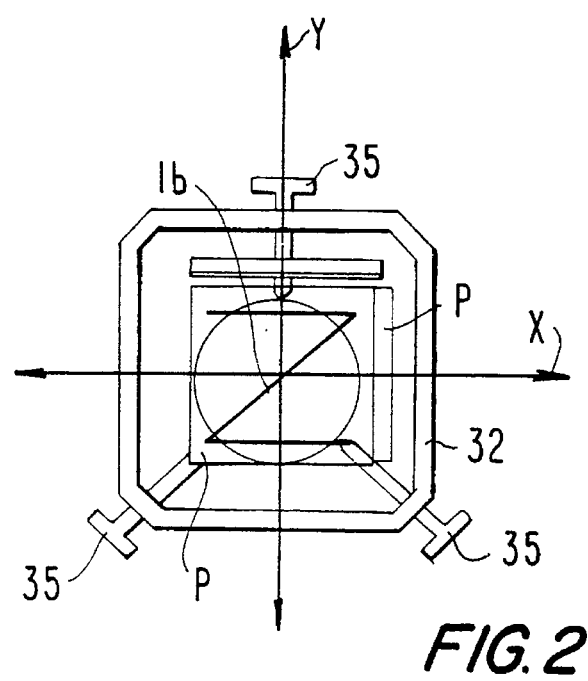
FIG. 2 is a diagrammatic top view showing radiopaque plates of the referential device of FIG. 1.
Figure 3:
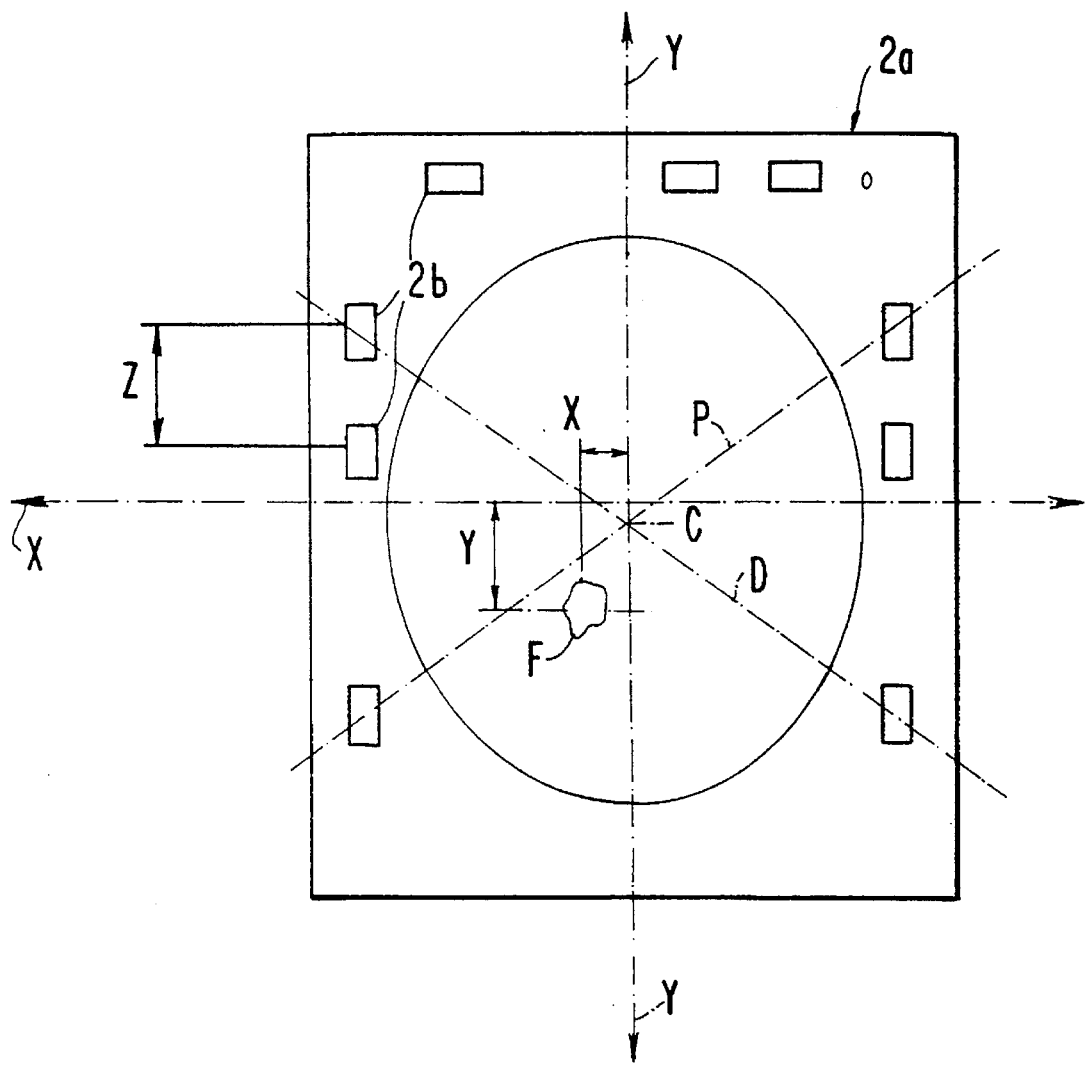
FIG. 3 is a two dimensional image or slice taken in a plane passing through the skull of a patient showing the position of a feature in the slice.

The stereotactic system of the invention also includes a referential device or devices for accurately determining a location of a point or feature F within the head H or skull based on a cartesian spatial coordinate system. A preferred embodiment of the referential device or devices is shown in FIGS. 1 to 3. The referential device includes two or three, advantageously square, radiopaque plates P, each of which are provided with a diagonal line 1b, the function of which is to determine, using magnetic resonance imaging (MRI) or computerized tomography (CT), the X, Y and Z coordinate positions of various features in the skull or head (See FIG. 3). As is well known these two techniques provide images with features and/or elements within the skull at well defined positions on a plane passing through the skull, i.e. the so-called slices 2a through the skull. The position of the point of intersection of the slice with the diagonal line or lines 1b on the plate P is shown on the slice 2a which provides a position reference.

When the examination to determine the location of the features or elements within the skull is undertaken the referential device is positioned with the plates P on lateral and front sides of the patient's skull in the case of the skull as shown in FIGS. 1 and 2. The plates P are, for example, secured to the square frame 3a as in FIG. 1. The center of the frame is determined by crossing lines D drawn between opposite intersection points on the slice 2a found by tomography, magnetic resonance or X-ray techniques. Once the center C of the frame is located on the slice 2a, it is possible to establish the X and Y axes and, measuring the distance from the axes to location of the feature F in the slice 2a, it is possible to arrive at the X, Y and Z coordinates of the feature F.

In operation the stereotactic system with the surgical tool mounted on it may be positioned in any of a number of different ways according to the directions of the surgeon. A lateral approach, a transphenoidal approach and a posterior fossa approach may be numbered among these possible positions. After positioning and determining the location within the skull to reached by the surgery, the equipment is assembled, the appropriate cannula, endoscope or laser ray device is mounted on the slider and, by correct positioning of the aforesaid surgical tool using the graduated scales, the drilling to the predetermined location within the skull takes place.

Since the system is isocentric, determination of the settings for the surgical tool is greatly simplified and the system is easier to learn and use.

While the invention has been illustrated and described as being embodied in a stereotactic system for surgical procedures, particularly in the cephalic and cervical regions, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A stereotactic system for surgical procedures, said stereotactic system comprising:

a frame (3a) securable around and to a head of a patient with a plurality of fixing screws (3s), said fixing screws (3s) circumferentially distributed around and passing through said frame (3a);

a vertical bar bracket (3c) releasably attachable to said frame (3a) according to at least one predetermined X- or Y-position in the head of the patient established by the surgical procedure;

a vertical graduated bar (3d) movably engaged with, and securable to the vertical bar bracket (3c), according to at least one predetermined Z-position in the head of the patient established according to the surgical procedure;

a graduated tube (3e) fixed to and extending perpendicularly from the graduate bar (3d);

a circular arc-shaped member (3f) provided with an angular positioning scale (AS) graduated in degrees, said circular arc-shaped member (3f) being releasably securable to and pivotably mounted on said graduated tube (3e) extending perpendicularly from the graduate bar (3d); and means for releasably securing a surgical tool at a predetermined angular position on said circular arc-shaped member (3f) on said angular positioning scale.

2. The stereotactic system as define in claim 1, wherein said frame (3a) consists of a ring (3b) and a graduated ruler (R) mounted on said ring (3b) so as to be perpendicular to a center axis of said ring (3b), and said vertical bar bracket (3c) is releasably attached to said graduated ruler (R).

3. The stereotactic system as define in claim 1, wherein said frame (3a) includes extension bars (4a) extending perpendicular to a plane of said frame (3a), said screws passing through end portions of said extension bars (4a) remote from said plane.

4. The stereotactic system as define in claim 1, further comprising a plurality of substantially square radiopaque plates, each of said square radiopaque plates being provided with diagonal lines and being mountable on said frame (3a), for eliminating complex mathematical calculations for positioning said surgical tool during said surgical procedure.

5. The stereotactic system as define in claim 1, wherein said means for releasably securing said surgical tool to said angular position on said circular arc-shaped member comprises a slider for holding said surgical tool and said slider is formed to hold at least one of a cannula, a retractor spatula, an arch for guided surgery and a laser tool.

* * * * *